United States Patent
Wang et al.

(10) Patent No.: US 10,937,531 B1
(45) Date of Patent: Mar. 2, 2021

(54) SYSTEM AND METHOD FOR TIMELY NOTIFICATION OF TREATMENTS TO HEALTHCARE PROVIDERS AND PATIENT

(71) Applicant: IQVIA Inc., Danbury, CT (US)

(72) Inventors: Yunlong Wang, Malvern, PA (US); Emily Zhao, Wayne, PA (US); Yilian Yuan, North Wales, PA (US); Anthony Michael Wojeck, Glenside, PA (US); Robert Doyle, Bryn Mawr, PA (US); Yong Cai, Bala Cynwyd, PA (US)

(73) Assignee: IQVIA Inc., Parsippany, NJ (US)

( * ) Notice: Subject to any disclaimer, the term of this patent is extended or adjusted under 35 U.S.C. 154(b) by 394 days.

(21) Appl. No.: 15/948,006

(22) Filed: Apr. 9, 2018

(51) Int. Cl.
*G16H 20/10* (2018.01)
*G16H 80/00* (2018.01)
*G16H 10/60* (2018.01)

(52) U.S. Cl.
CPC ............. *G16H 20/10* (2018.01); *G16H 10/60* (2018.01); *G16H 80/00* (2018.01)

(58) Field of Classification Search
CPC .................................................... G16H 20/10
See application file for complete search history.

(56) References Cited

U.S. PATENT DOCUMENTS

| | | | |
|---|---|---|---|
| 6,286,005 B1 * | 9/2001 | Cannon | G06Q 30/02 455/2.01 |
| 6,334,110 B1 * | 12/2001 | Walter | G06Q 30/02 705/14.41 |
| 2009/0265316 A1 * | 10/2009 | Poulin | G06Q 50/22 |
| 2009/0287837 A1 | 11/2009 | Felsher | |
| 2013/0159021 A1 | 6/2013 | Felsher | |
| 2014/0052475 A1 | 2/2014 | Madan | |
| 2014/0081669 A1 | 3/2014 | Raduchel | |
| 2014/0357961 A1 | 12/2014 | Meltzer | |
| 2015/0046192 A1 | 2/2015 | Raduchel | |
| 2015/0134346 A1 | 5/2015 | Hyde | |
| 2015/0244687 A1 | 8/2015 | Perez | |
| 2015/0269355 A1 | 9/2015 | Tidor | |
| 2017/0161439 A1 | 6/2017 | Raduchel | |

FOREIGN PATENT DOCUMENTS

KR 2009009006 * 1/2009 ............. G06Q 30/00

* cited by examiner

*Primary Examiner* — John A Pauls
(74) *Attorney, Agent, or Firm* — Fish & Richardson P.C.

(57) ABSTRACT

A computer-assisted method to provide timely multi-channel notification of treatments to healthcare providers and patients, the method including receiving de-identified longitudinal medical records, treatment prescription records of healthcare providers, and notification data. Relationships between the healthcare providers, the anonymized patients, and the notifications are identified using the de-identified longitudinal medical records, the treatment prescription records of the healthcare providers, and the notification data. An impact of notifications being received by both the healthcare provider for the anonymized patient and the anonymized patient on whether the anonymized patient received the treatment is determined. A plan to timely provide notifications of treatments to the healthcare provider and the anonymized patients is determined based at least on the impact of the notifications being received by both the healthcare provider for the anonymized patient and the anonymized patient on whether the anonymized patient received the treatment.

20 Claims, 7 Drawing Sheets

FIG. 6 ved to both patients and healthcare providers on whether a treatment was received by a patient may have been impossible.

SYSTEM AND METHOD FOR TIMELY NOTIFICATION OF TREATMENTS TO HEALTHCARE PROVIDERS AND PATIENT

BACKGROUND

Medical patients may receive various treatments. For example, a medical patient may be prescribed medication by a healthcare professional.

TECHNICAL FIELD

This disclosure relates to providing notifications regarding treatments.

SUMMARY

Timely providing notifications regarding treatments to patients and healthcare providers may result in more patients receiving a treatment. For example, some patients and healthcare providers may have been unaware of the availability of the treatment or benefits of the treatment until receiving the notifications. However, providing notifications to healthcare providers and patients may consume resources. For example, processing power, storage capacity, and monetary resources may be needed to provide notifications.

Different notifications may have different impacts on patients and healthcare providers. For example, a first notification may be associated with a large amount of storage usage but have a low impact on a patient receiving treatment, a second notification may be associated with a moderate amount of storage usage but have a high impact on a patient receiving a treatment, and a third notification may be associated with a high amount of storage usage but have a moderate impact on a patient receiving a treatment. Accordingly, in this example, providing more of the second notification may be helpful in view of balancing storage usage and impact. In another example, the processing needed in providing notifications based on using notifications that result in greater impact and lesser processing usage. It should be understood that these are simple examples.

Determining an impact of notifications provided to patients and healthcare providers regarding treatments may be problematic. For example, it may be difficult to determine whether a patient receiving a treatment was a result of only a first notification to the patient, a result of only a second notification to the patient, a result of both the first notification and the second notification to the patient, a result of only a notification to the healthcare provider of the patient, a result of both of the notifications to the patient and the notification to the healthcare provider of the patient, or a result of none of the notifications. Additionally, there may be significant problems in determining an impact of a notification about a treatment provided to a patient or healthcare provider on a receipt of the treatment by the patient as, in healthcare, treatments generally do not immediately follow notifications of treatments. For example, a patient may not get a prescription without a doctor, the doctor may recommend other lifestyle changes, other treatments, order tests, etc. before prescribing the patient a drug, the patient then may need to go to the pharmacy to get the prescribed drug. Additionally, the patient may need to have insurance or some other way to supplement the expense of the prescribed drug before making the purchase. Additionally, in healthcare, patient information generally must be anonymized. Conventionally, determining the impact of notifications pro- A system that provides timely notification of treatments to healthcare providers and patients may determine the impact of the various notifications to determine a plan to provide notifications to healthcare providers and patients that increases the amount of patients that receive the treatment. The system may use the impacts of various notifications to generate a plan for providing notifications in the future, and then provide notifications according to the plan. As such, the described techniques may enable a computer to perform operations that the computer was previously unable to perform due to challenges with determining the impact of notifications on healthcare providers and patients.

In one aspect, some implementations provide a computer-implemented method that includes actions of receiving, from one or more database systems each comprising non-volatile data storage devices, de-identified longitudinal medical records, each de-identified longitudinal medical record representing a record of a different anonymized patient and encoding information identifying a treatment received by the anonymized patient, information identifying a time the treatment was received, and an identifier that uniquely distinguishes the anonymized patient from other anonymized patients, the records devoid of information identifying the patients; receiving, from one or more database systems each comprising non-volatile data storage devices, treatment prescription records of healthcare providers, each treatment prescription record representing prescription of a treatment to an anonymized patient and encoding information identifying a treatment prescribed by the healthcare provider, an identifier of the healthcare provider, and the identifier that uniquely distinguishes the anonymized patient from other anonymized patients; receiving, from one or more database systems each comprising non-volatile data storage devices, notification data including notification records, each notification record encoding information identifying a channel through which a notification for the treatment was provided, information identifying a time the notification was received, and information referring to a recipient that received the notification; identifying relationships between the healthcare providers, the anonymized patients, and the notifications using the de-identified longitudinal medical records, the treatment prescription records of the healthcare providers, and the notification data; determining, based at least on the notification records and the relationships identified between the healthcare providers and the anonymized patients, an impact of notifications being received by both the healthcare provider for the anonymized patient and the anonymized patient on whether the anonymized patient received the treatment; and determining a plan to timely provide notifications of treatments to the healthcare provider and the anonymized patients based at least on the impact of the notifications being received by both the healthcare provider for the anonymized patient and the anonymized patient on whether the anonymized patient received the treatment.

Implementations may include one or more of the following features. In certain aspects, identifying relationships between the healthcare providers, the anonymized patients, and the notifications using the de-identified longitudinal medical records, the treatment prescription records of the healthcare providers, and the notification data includes identifying that the identifier that uniquely distinguishes the anonymized patient from other anonymized patients in a particular de-identified longitudinal medical record matches the identifier that uniquely distinguishes the anonymized patient from other anonymized patients in a particular treatment prescription record.

In some aspects, determining, based at least on the notification records and the relationships identified between the healthcare providers and the anonymized patients, an impact of notifications being received by both the healthcare provider for the anonymized patient and the anonymized patient on whether the anonymized patient received the treatment includes determining a patient impact model based on the notification records of notifications provided to anonymized patients and the de-identified longitudinal medical records; determining healthcare provider related parameters for a joint patient-healthcare provider impact model using the patient impact model, the notification records, and the treatment prescription records of the healthcare providers; and determining patient related parameters for the joint patient-healthcare provider impact model using the notification records, the de-identified longitudinal medical records, and the healthcare provider related parameters. In some implementations, determining the healthcare provider related parameters and the patient related parameters are sequentially iterated multiple times.

In certain aspects, determining, based at least on the notification records and the relationships identified between the healthcare providers and the anonymized patients, an impact of the notifications being received by both the healthcare provider for the anonymized patient and the anonymized patient on whether the anonymized patient received the treatment includes providing the notification records, information indicating the relationships identified between the healthcare providers and the anonymized patients to a machine-learning graphical model to output a joint patient-healthcare provider impact model. In some aspects, determining a plan to timely provide notifications of treatments to the healthcare provider and the anonymized patients based at least on the impact of notifications being received by both the healthcare provider for the anonymized patient and the anonymized patient on whether the anonymized patient received the treatment includes obtaining information describing notification constraints; obtaining information describing resources necessary to provide notifications through respective channels to patients; obtaining information describing resources necessary to provide notifications through respective channels to healthcare providers; and determining the plan based at least on the information describing notification constraints, information describing resources necessary to provide notifications through respective channels to patients, the information describing resources necessary to provide notifications through respective channels to healthcare providers, and the impact of the notifications being received by both the healthcare provider for the anonymized patient and the anonymized patient on whether the anonymized patient received the treatment.

In some implementations, receiving treatment prescription records of healthcare providers is in response to providing a request for treatment prescription records of healthcare providers with particular attributes. In certain aspects, receiving the de-identified longitudinal medical records is in response to providing a request for de-identified longitudinal medical records of patients with particular attributes. In some aspects, the notification records encode information identifying notifications provided through channels including a digital channel and a non-digital channel. In some implementations, actions include scheduling, based at least on the plan, a first set of notifications to be provided through respective channels to only the patients, a second set of notifications to provided through respective channels to only the healthcare providers, and a third set of notifications to be provided to both the healthcare providers and the patients.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

Like reference symbols in the various drawings indicate like elements.

DETAILED DESCRIPTION

Figure 1A:
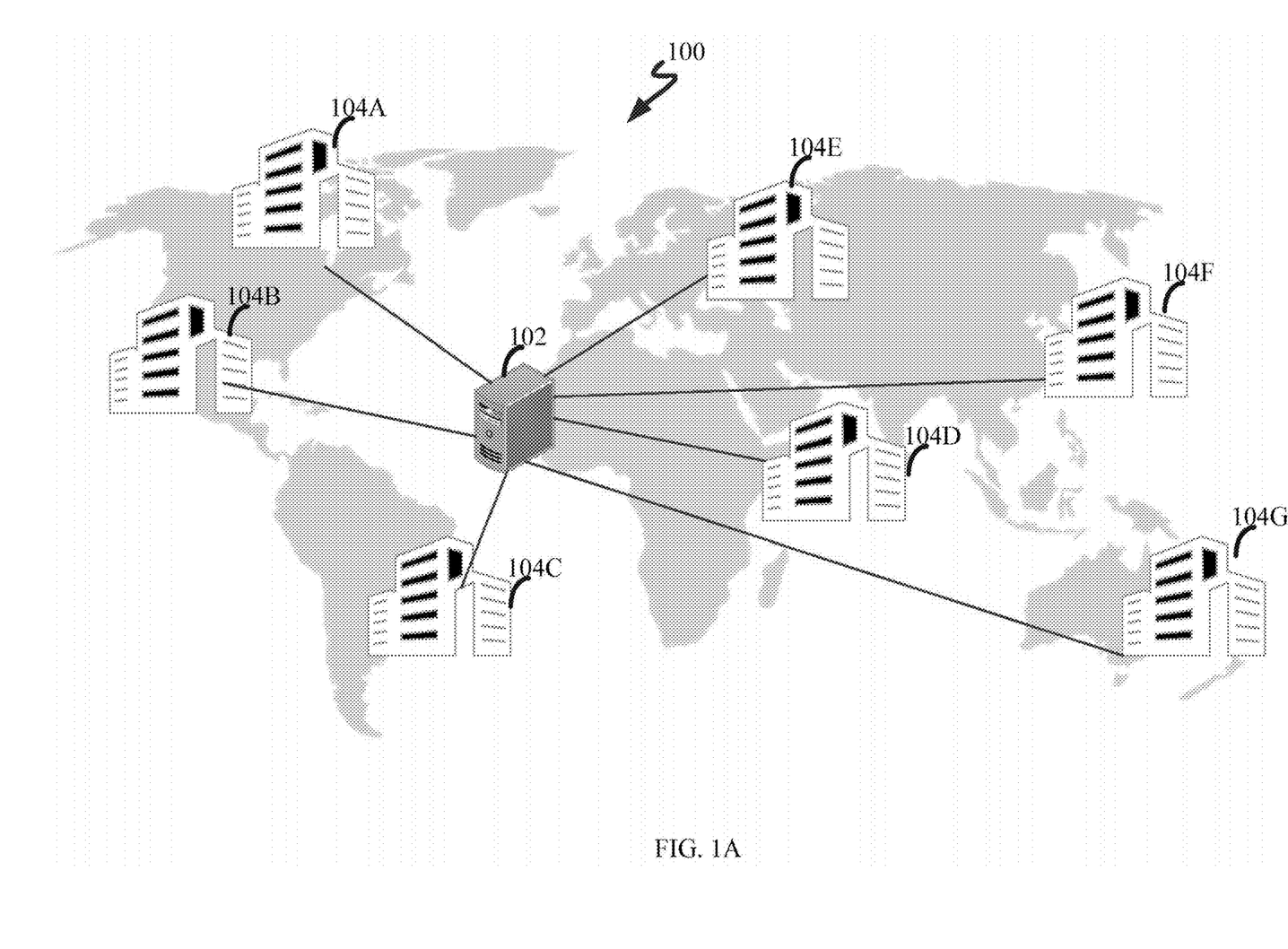
FIG. 1A illustrates an example of a system for deriving de-identified longitudinal medical data from various data supplier sites.

FIG. 1A illustrates an example system 100 for obtaining de-identified longitudinal medical records. In some implementations, de-identified longitudinal medical records may be collected from data servers at healthcare providers that record filled prescription information, medical operations, doctor visits, or other medical events for patients. The information may generally include records of different anonymized patients, where each record identifies one or more treatments received by the anonymized patient, the one or more times the treatments were received by the anonymized patient, and an identifier that uniquely distinguishes the anonymized patient from other anonymized patients. The identifier may refer to a de-identified patient, which may also be referred to as an anonymized patient. The de-identification means no identity information, such as name, address, birth date, or social security information, is available in the recorded information. Instead, each patient is referenced by an anonymous tag that is specific to the patient. Accordingly, an anonymized patient may be a patient for which the patient's identity cannot be determined but is distinguishable from other anonymized patients. Generally, the anonymous tag is doubly encrypted using a key specific to a data supplier (such as a data server at a pharmacy) and another key specific to a longitudinal database.

The medical records may include treatment data in the form of prescription data. The prescription may include a pharmaceutical product such as a prescription drug approved by a regulatory agency, such as the Federal Drug Administration (FDA), the European Medicines Agency (EMA), the Medicines and Healthcare products Regulatory Agency (MHRA). The pharmaceutical product can also include approved medical devices. The prescriptions may be filled at multiple sites, such as pharmacies 104A to 104G. These sites can cover a geographic region, for example, a region in a particular country. These sites may also be located globally, for example, the North American continent, or the European Union.

Prescription data for each participant patient may be collected from each pharmacy store. In one example, a pharmacy database may collect prescription data from all pharmacy stores on a daily basis. The pharmacy database includes non-volatile data storage devices. Each pharmacy store may house its own data server in communication with the pharmacy database to transfer prescription data on a daily basis. The prescription data records the information about a particular prescription when the prescription was filled. As disclosed herein, the prescription data for each participant patient, as recorded at the pharmacy store at the time of filling, is de-identified such that the data does not include information capable of identifying the particular participant patient. Examples of such identifying information include: patient's name, patient's insurance identification number, patient's Medicare/Medicaid identification number, patient's social security number, patient driver's license number, etc. In some implementations, such identifying information may be converted by a one-way hash-function to generate an alpha-numerical string. The alpha-numerical string conceals the identity of the individual participant patient, thereby maintaining confidentiality of the data as the data is being reported, for example, daily from the sites 104A to 104G to the central server 102. There, data corresponding to the same participant patient may be linked by virtue of the matching alpha-numerical string. Thus, data for the same participant patient may be longitudinally tracked for each individual, without compromising confidentiality of the individual patients, even though the patient can fill the prescription at various stores and the patient can receive a prescription for a healthcare product from various healthcare professionals.

Additionally or alternatively, the de-identified longitudinal medical records may include other forms of data. For example, the de-identified longitudinal medical records may include data describing operations performed on a patient and when the operations were performed, when a patient made a visit to a particular doctor, when a doctor performed a diagnosis on a patient, and other events. In these instances, the sites may be healthcare providers that include pharmacy stores and other types of healthcare providers, e.g., doctor's offices or hospitals.

Reconciling disparate records from across different databases can be computationally burdensome to the extent that many desirable database operations are precluded across large and complex databases. For example, in the health care field, a variety of epidemiological studies would reveal links between disparate events. These problems are particularly acute in that the underlying databases may be de-identified in order to satisfy medical privacy concerns. Further, the size of the databases, which can include complex coding for complex and disparate diagnoses may make establishing links between different events even more computationally intensive as a specified item may be compared against countless other items, diagnoses, stimuli, and conditions. These operations are further complicated by different data sources that are formatted in different conventions and with varying degrees of completeness. Further, databases may be constantly updated with large volumes of new information. Thus, newly-received records must be reconciled with and compared to existing records and databases in order to ascertain new trends and real-time information.

The problem is particularly acute where longitudinal data associated with a de-identified label is reconciled between two different data sources with two different time sequences that describe different and sometimes unrelated activity. In order to perform the requisite correlation between the two different data sources, the data must be formatted in a manner that facilitates ready comparison of two different data points from each of the data sources. Once rapid comparison of disparate sources can be relied upon, an organization, such as a Patient Safety Organization (PSO) can act in reliance upon the identified correlations and work to address the correlations and derived identifications. For example, one such correlation may be associated with a breach in the desired activity (e.g., a standard of care). A medical administrator then may work to identify these deviations as fault or alarm conditions and take corrective action in real-time. Note that the deviations need not formally be relative to some regulatory standard (e.g., the standard of care). Instead, the deviation may exist relative to desired behavior (e.g., an internal hospital policy).

Based on the architecture and organization, a variety of configurations may be used to facilitate analysis of patent records organized longitudinally according to a first timeline relative to another source of data organized according to a second timeline. The longitudinal data may be used for timely providing notifications of treatments to patients and healthcare providers.

Figure 1B:
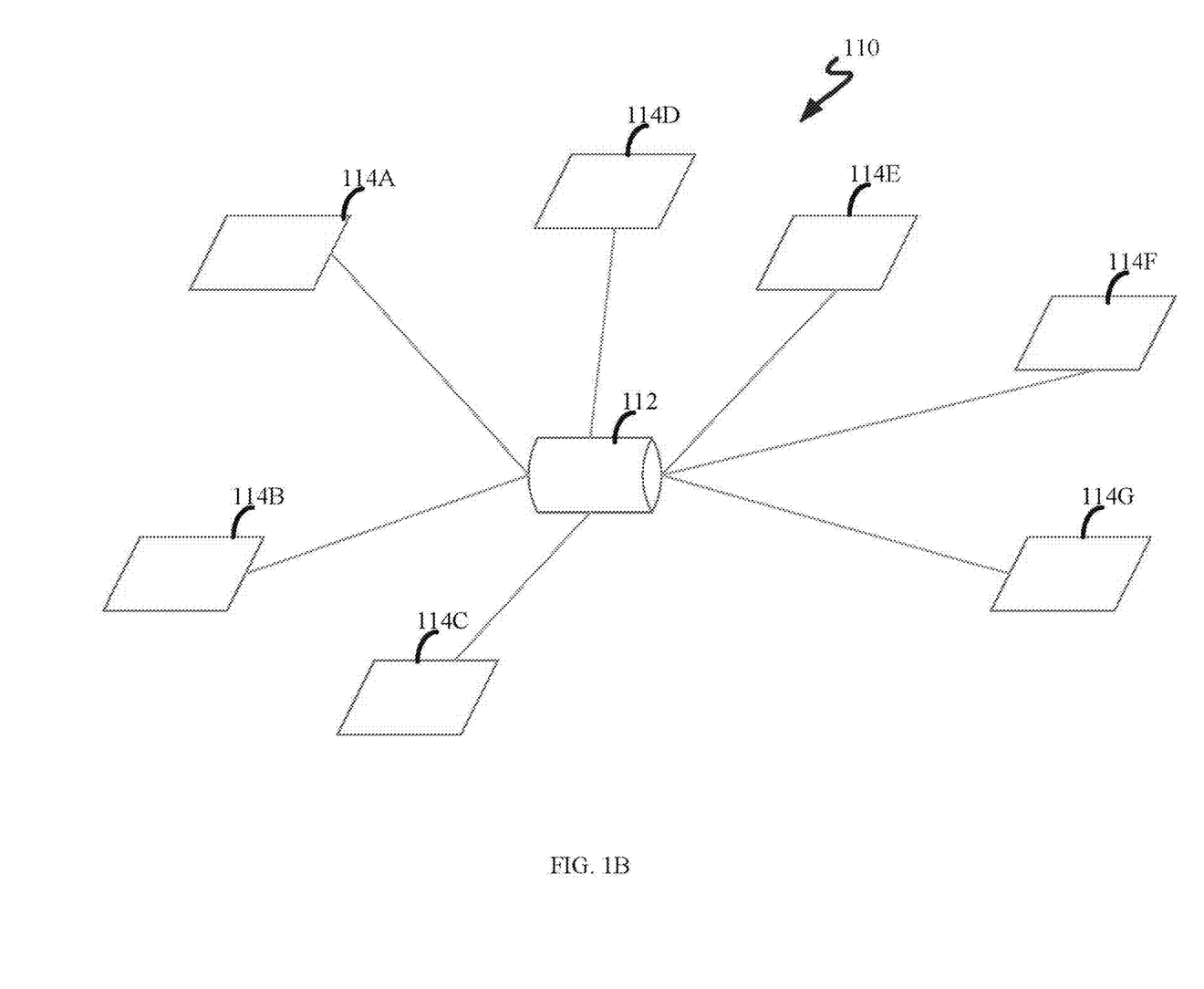
FIG. 1B illustrates an example of a system for aggregating medical data from data servers at healthcare providers longitudinally tracking the treatment pattern of human patients.

FIG. 1B illustrates an example work flow 110 for collecting data of patient recipients from data servers at various healthcare providers and longitudinally tracking the medical record of each individual patient recipient over time. Data 114A-114G may correspond to prescription data reported from each pharmacy store. In some implementations, data 114-114G may be reported from data servers at each pharmacy store on a daily basis, for example, at the end of business data local time. Data 114A-114G remain de-identified to preserve confidentiality, as disclosed herein. In this illustrated work flow, each pharmacy store may employ the same one-way hashing function to anonymize data records of each patient. As a result, reported prescription data 114A-114G, as received at central server 102 to update database 112, include the same de-anonymized key for prescription records from the same patient, even if the patient may move to another pharmacy store, another healthcare professional, or another healthcare provider (e.g., health insurance carrier, pharmacy insurance carrier). The central server 102 may match prescription data records from the same patient recipient to update database 112, which contains data records reported earlier for the same patient recipient.

In some implementations, however, the de-identified data may be further encrypted before the data is reported to central server 102 to update database 112. For illustration, data 114A-114G may be encrypted using a symmetric encryption key specific to each pharmacy store. The symmetric encryption key may only be known to the pharmacy store and central server 102. Thus, only the participant site can encrypt the de-identified data with the symmetric key and only the central server 102 can decrypt the encrypted de-identified data with the particular symmetric key. In another illustration, a public-key infrastructure (PKI) may be used such that the reported data may be encrypted with the public key of the central server 102 so that only the central server 102 can decrypt using its private key. In other illustrations, the central server 102 and pharmacies 104A-104G may exchange messages using the PKI to establish an agreed-on symmetric key.

As discussed above, the data 114A-114G may correspond to other data besides prescription data. For example, the data 114A-114G may describe operations performed on a patient and when the operations were performed, when a patient made a visit to a particular doctor, when a doctor performed a diagnosis on a patient, and other events received from healthcare providers that include pharmacy stores and other types of healthcare providers, e.g., doctor's offices or hospitals.

The de-identification process allows such prescription data to remain anonymous. In some implementations, the de-identified data from the same patient may be linked at central server 102. Data may be received on different days for the patient recipients. For example, on time point N, a first set of de-identified prescription data may be received. Likewise, on time point N+1, a second set of de-identified prescription data are received. Similarly, on time point N+2, a third set of de-identified data may be received. Each of these de-identified prescription data sets may include data that corresponds to different patient recipients. Based on matching tags, such as matching de-identified alpha-numerical strings, the de-identified prescription data from each patient recipient may be linked and hence the prescription activity of a particular patient recipient can be longitudinally tracked. In some implementations, the matching tags may include graphic representations as well as alpha-numerical strings. The graphic representations are also de-identified to remove personally identifiable information of the participant patient. In some instances, the alpha-numerical strings or graphical representations may be tags to the actual prescription data record, which may be referred to as part of the metadata. In other instances, the alpha-numerical strings or graphical representations may be embedded to the actual prescription data record itself. In still other instances, the alpha-numerical strings or graphical representations may be part of the metadata and embedded in the actual prescription data record. The implementations of both the tag and the embedding may further deter alterations or modifications of the data records being reported from each participant site. When the received daily data records are linked with earlier data records of the same patient recipients, database 112 may be updated. The updated database may allow a variety of data analytics to be generated, revealing the interesting insights of prescription usage pattern for each patient recipient as well as the statistical prescription pattern of each healthcare professional, as discussed below.

As discussed above, the de-identified prescription data may correspond to other de-identified data besides prescription data. For example, the de-identified data may describe operations performed on a patient and when the operations were performed, when a patient made a visit to a particular doctor, when a doctor performed a diagnosis on a patient, and other events.

Figure 2:
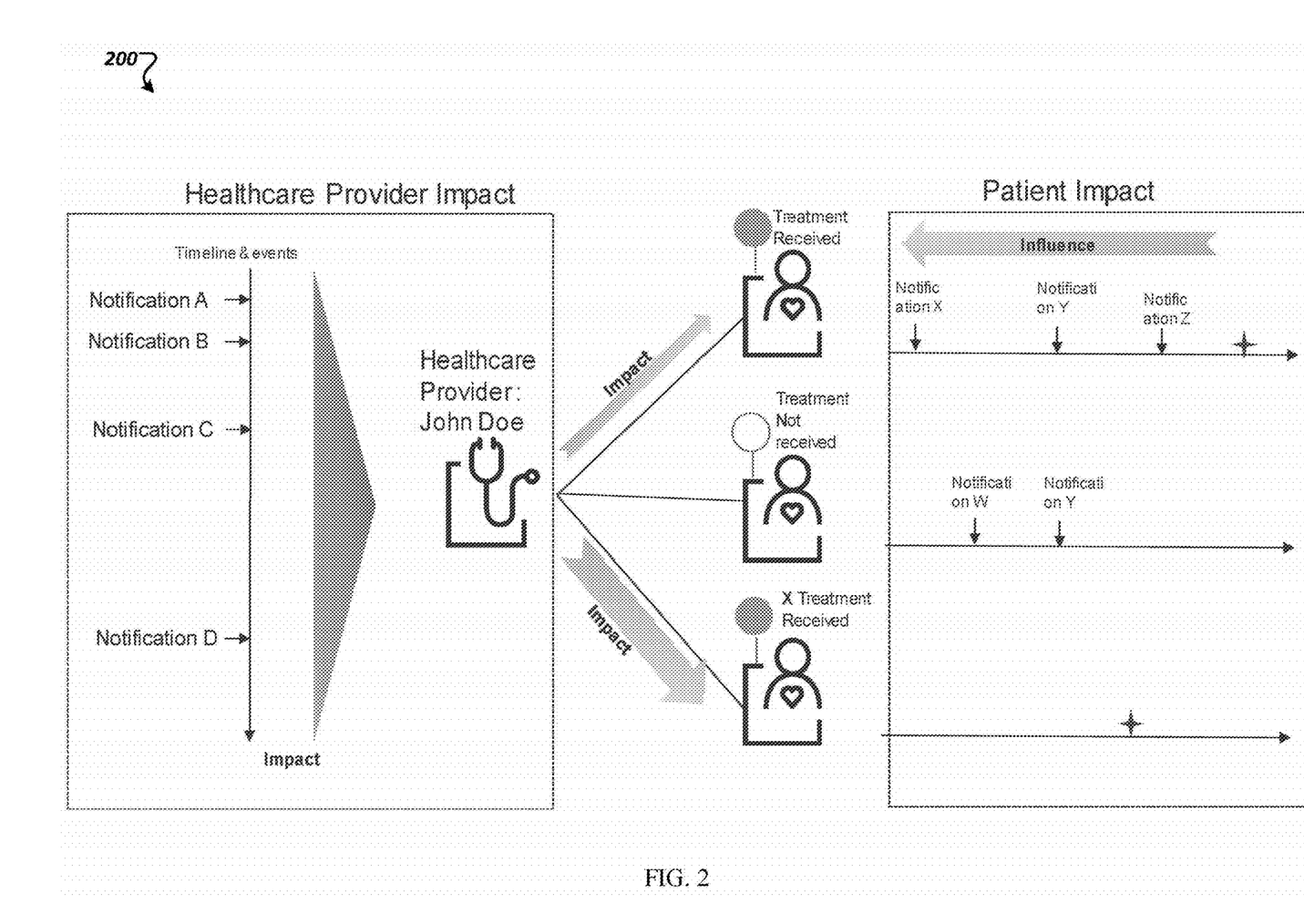
FIG. 2 illustrates an example scenario of impacts of notifications on healthcare providers and patients.

FIG. 2 illustrates an example scenario of impacts of notifications on healthcare providers and patients. As shown in scenario 200, a health care provider, John Doe, may receive different notifications regarding a treatment at different times and patients of the healthcare provider may independently and variously receive different notifications regarding the treatment at different times. For example, healthcare provider John Doe may receive Notification A identifying a particular treatment at a first time, Notification B identifying the particular treatment at a second time after the first time, Notification C identifying the particular treatment at a third time after the second time, and Notification D identifying the particular treatment at a fourth time after the third time.

The scenario 200 further shows how a first patient may receive Notification X identifying the particular treatment at a fifth time, receive Notification Y identifying the particular treatment at a sixth time after the fifth time, receive Notification Z identifying the particular treatment at a seventh time after the sixth time, and then receive the particular treatment itself. A patient receiving a particular treatment may refer to a patient filling a prescription. For example, while a healthcare provider may prescribe a drug to a patient, the patient may not be considered as receiving the drug until the patient fills the prescription for the drug. It may be difficult to determine the impact of each the Notifications A, B, C, D to the healthcare provider and Notifications X, Y, Z provided to the patient on the patient receiving the particular treatment. For example, some healthcare providers may not listen to patients regarding a type of treatment the patient wishes to receive and only prescribe treatments the healthcare providers believe is most appropriate, other healthcare providers may give great deference to patients regarding the type of treatment the patient wishes to receive, some patients may greatly defer to healthcare providers on what treatments they receive, and some other patients may not give much deference to healthcare providers on what treatments they receive.

The scenario 200 further shows how a second patient may receive Notification W identifying the particular treatment at an eighth time, receive Notification Y identifying the particular treatment at the sixth time after the eighth time, and then not receive the particular treatment itself. Accordingly, when considering the second patient in combination with the first patient, the notifications of X and Z may have a greater impact as receipt of those notifications by the first patient and not the second patient may possibly have resulted in the first patient receiving the treatment and the second patient not receiving the treatment.

The scenario 200 further shows how a third patient may receive no notifications and then receive the particular treatment itself. Accordingly, in considering the various patients of the healthcare provider together, the notifications provided to the healthcare provider may generally have greater impact than notifications provided to the patients, however notifications X and Z may still have a large impact.

Figure 3:
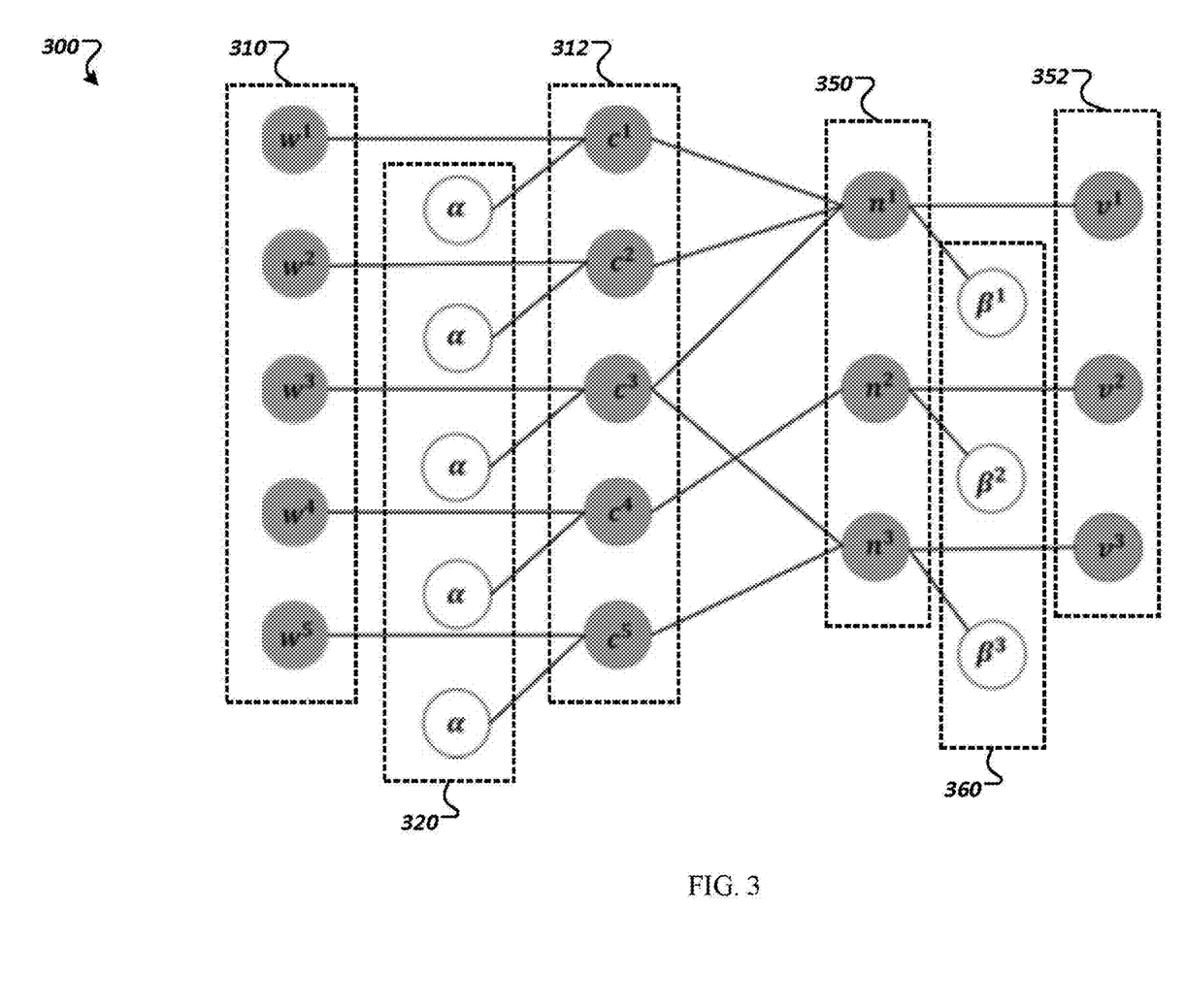
FIG. 3 illustrates an example of a model of impacts of notifications on healthcare providers and patients.

FIG. 3 illustrates an example of a model 300 of impacts of notifications on healthcare providers and patients. The model 300 may include nodes representing notifications to patients 310, nodes representing patient related parameters regarding impact of notifications 320, nodes representing whether a patient received the treatment 312, nodes representing whether a healthcare provider prescribed the treatment 350, nodes representing healthcare provider related parameters regarding impact of notifications 360, and nodes representing notifications to healthcare providers 352. The value for nodes representing notifications to patients 310, value for nodes representing whether a patient received the treatment 312, value for nodes representing whether a healthcare provider prescribed the treatment 350, and value for nodes representing notifications to healthcare providers 352 may be observed from various records and databases. The values for nodes representing patient related parameters regarding impact of notifications 320 and values for nodes representing healthcare provider related parameters regarding impact of notifications 360 may be estimated from the values of nodes 310, 312, 350, and 352 which are observed.

Figure 4:
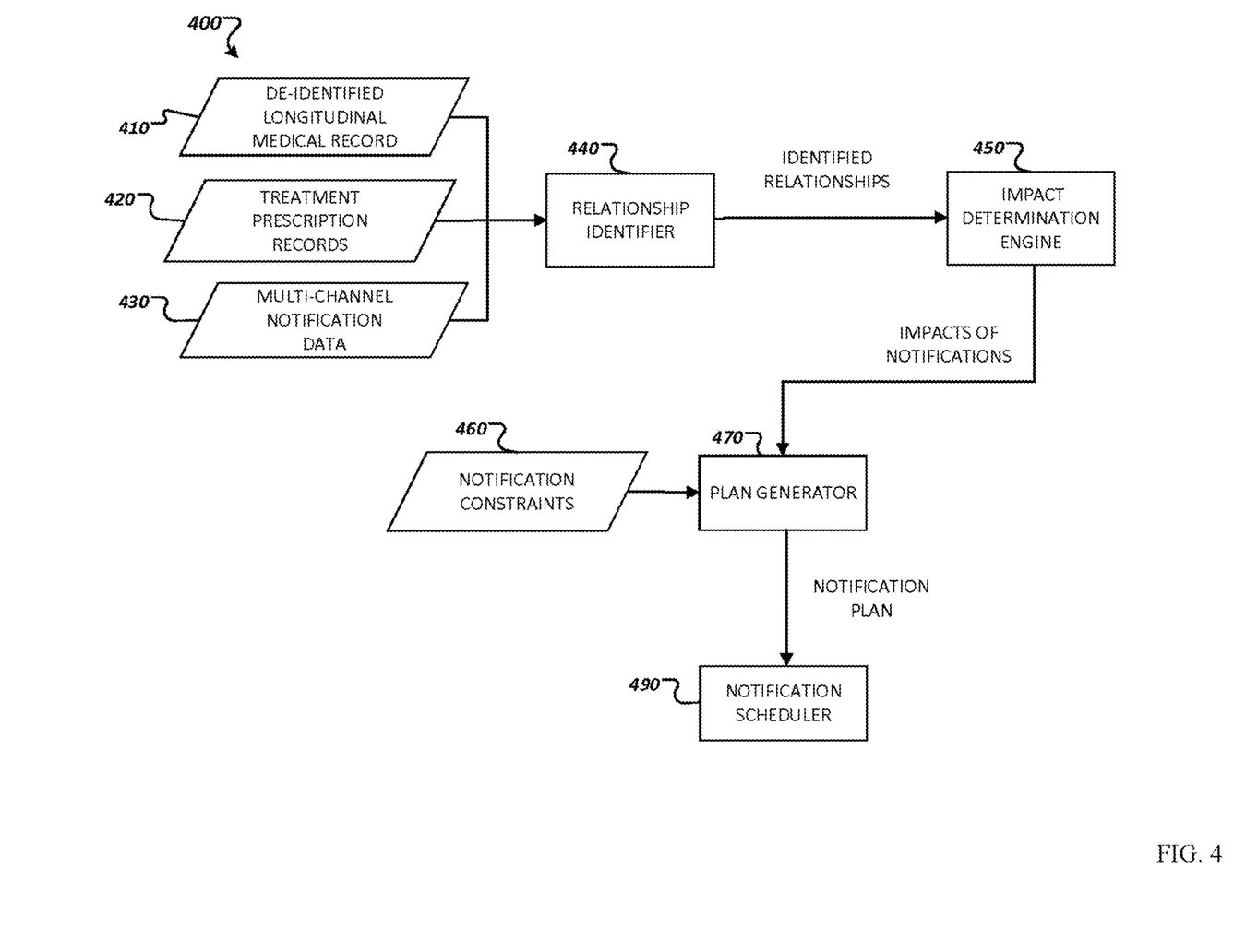
FIG. 4 illustrates an example of a block diagram of a system for providing timely notification of treatments to healthcare providers and patients.

FIG. 4 illustrates an example of a block diagram of a system 400 for providing timely notification of treatments to healthcare providers and patients. The system 400 may include a relationship identifier 440 that identifies relationships between de-identified longitudinal medical records, treatment prescription records, and notification data, an impact determination engine 450 that determines impacts of notifications based on the identified relationships, a plan generator 470 that determines a notification plan based on the impacts of notifications, and a notification scheduler 490 that schedules notifications based at least on the notification plan.

In more detail, the relationship identifier 440 may identify relationships between the de-identified longitudinal medical records 410, treatment prescription records 420, and the notification data 430. As described above, the de-identified longitudinal medical records 410 may be collected from data servers at healthcare providers that record filled prescription information, medical operations, doctor visits, or other medical events for patients. The records 410 may generally include records of different anonymized patients, where each record identifies one or more treatments received by the anonymized patient, the one or more times the treatments were received by the anonymized patient, and an identifier that uniquely distinguishes the anonymized patient from other anonymized patients.

The treatment prescription records 420 may similarly be collected from data servers at healthcare providers that record prescriptions made by healthcare providers. The records 420 may generally include records of different healthcare providers, where each record identifies a treatment prescribed to an anonymized patient, a date that the treatment was prescribed, a healthcare provider that prescribed the treatment, and an identifier that uniquely distinguishes the anonymized patient from other anonymized patients.

The notification data 430 may be collected from data servers of notification providers that record notifications provided to recipients. A notification may include text, one or more images, one or more videos, or one or more audio identifying a treatment. The notifications may be placed in various locations, e.g., on websites, television advertisements, in mobile applications, or radio broadcasts. For example, a first type of notification may be provided through a digital channel, e.g., through a website or the Internet, and a second type of notification may be provided through a non-digital channel, e.g., television or radio. Accordingly, the notification data 430 may be considered multi-channel notification data as it indicates notifications being provided through different channels. Different types of notifications may also be provided through a channel. For example, a first type of notification may be provided with an image on a website and a second type of notification may be provided with text on the web site.

The notification data may include notification records that each identify a type of notification provided, a time the notification was received, and the recipient of the notification. As described above, the type of notification may include an indication of one or more of a channel for the notification, a subchannel for the notification, and the notification itself. For example, the indication may indicate that an image-based notification was provided through a non-digital television channel and a particular subchannel of "Channel 5" and a text-based notification was provided through a digital online channel and a particular subchannel of "Health.com." The notification data may include notification records that each identify a type of notification provided, a time the notification was received, and the recipient of the notification. Recipients of notifications may include patients and healthcare providers. For example, notification data may indicate a first notification identifying a treatment was received by a healthcare provider at a first time and a second notification identifying the same treatment was received by a patient of the healthcare providers at a second time.

In some implementations, the relationship identifier 440 may reduce an amount of data needed to be transferred, stored, and processed based on requesting records and notification data matching particular attributes and then only receiving records and notification data corresponding to those attributes. For example, a user of the system 400 may desire to timely provide notifications to patients and healthcare providers located within a particular area. The relationship identifier 410 may then provide a request to databases storing the records and notification data for records corresponding to patients or healthcare providers located within that particular area. In another example, the relationship identifier 410 may provide a request for only medical records of patients that received a particular treatment for which the impact of notifications on the particular treatment being received is to be determined.

To determine the impact of notifications on the particular treatment, the relationship identifier 440 may build a factor graphical model with machine learning techniques. The model may be data-driven and agent-based, in which not only patient but also channel level notifications and records are leveraged as the input of the model, and the output is the attribution of each notification to the treatment. In more detail, the relationship identifier 440 may learn an optimized function that best reflects the relationship between the total treatments and various notifications. Mathematically, the model may set up total treatments as the dependent variable and multi-channel notifications as independent variables. Given treatment data and multi-channel notification datasets, this model may be trained through non-negative least square method. The training objective function may be biconvex, therefore the alternating minimization applied in the training algorithm may guarantee convergence to a stationary point.

The model may address both the notification lag and channel interaction effects in multi-channel notifications. In modeling the lagged effect of a notification on health care provider and patient's treatment choice, exponential factors may be used where it is assumed that exposure to notifications builds awareness and this awareness will exponentially decay to negligible levels as time goes on. To account for channel interactions, the relationship identifier 440 may use a collaborative filtering based concept, in which the combination terms are incorporated in the model using Kronecker-product of notifications from multiple channels.

The relationship identifier 440 may obtain the de-identified longitudinal medical records 410, the treatment prescription records 420, and the notification data 430, and identify relationships between anonymized patients, the healthcare providers of anonymized patients, and recipients. For example, the relationship identifier 440 may identify that a particular anonymized patient received a first notification, a healthcare provider of the particular anonymized patient also received a second notification, the healthcare provider prescribed the treatment after receiving the second notification, and the anonymized patient received the treatment. In another example, the relationship identifier 440 may identify that a particular anonymized patient received the first notification, a healthcare provider of the patient did not receive the second notification, the healthcare provider prescribed the treatment, and the anonymized patient received the treatment. In yet another example, the relationship identifier 440 may identify that a particular anonymized patient did not receive the first notification, a healthcare provider of the patient received the second notification, the healthcare provider prescribed the treatment after receiving the second notification, and the anonymized patient did not receive the treatment.

The relationship identifier 440 may identify relationships based on determining whether identifiers that uniquely distinguishes the anonymized patient from other anonymized patients in the de-identified longitudinal medical records 410, the treatment prescription records 420, and the notification data 430 match. For example, the relationship identifier 440 may determine that a particular anonymized patient is a patient of a particular healthcare provider based on determining that an identifier that uniquely distinguishes the anonymized patient from other anonymized patients in the medical records 410 of the anonymized patient matches an identifier that uniquely distinguishes the anonymized patient from other anonymized patients in the treatment prescription records 420.

The relationship identifier 440 may similarly identify relationships between anonymized patients and recipients of notifications, and healthcare providers that prescribe treatments and recipients of notifications. For example, the relationship identifier 440 may identify from a medical record that an anonymized patient identified as "ad978zfvd3426oiu90" received a particular treatment, identify from the notification data that a recipient identified as "ad978zfvd3426oiu90" received a notification for the particular treatment, and that the identifiers both have the value "ad978zfvd3426oiu90." In some implementations, the relationship identifier 440 may, one or more of, determine whether notification records are for notifications for other treatments and determine to ignore those notifications or determine whether treatments indicated by the medical records are for other treatments and determine to ignore those indications in the medical records.

The impact determination engine 450 may determine impacts of notifications based on the relationships identified by the relationship identifier 230. For example, the impact determination engine 450 may determine that a first notification provided to some patients had a low impact on patients receiving a treatment and a second notification provided to some healthcare providers had a high impact on patients receiving a treatment. The impact determination engine 450 may determine impacts of notifications through a model of impacts of notifications on healthcare providers and patients. For example, the impact determination engine 450 may determine the values of the nodes 320, 360 from the values of the nodes 310, 312, 350, and 352 as indicated by the relationships identified by the relationship identifier 440.

The impact determination engine 450 may determine the impact of notifications based on initially determining a patient impact model based on the notification records of notifications provided to anonymized patients and the de-identified longitudinal medical records, determining healthcare provider related parameters for a joint patient-healthcare provider impact model using the patient impact model, the notification records, and the treatment prescription records of the healthcare providers, and determining patient related parameters for the joint patient-healthcare provider impact model using the notification records, the de-identified longitudinal medical records, and the healthcare provider related parameters. For example, the impact determination engine 450 may determine the patient impact model by determining the values of the nodes 360 when ignoring the nodes 310, 312, and 312, then determine the values of nodes 320 when taking into account the values just determined for nodes 360 and the values for nodes 310, 312, 350, and 352, and then determining updated values for nodes 360 based on the most recently determined values for nodes 320 and values of nodes 310, 312, 350, and 352. The impact determination engine 450 may determine the patient related parameters using a stochastic gradient descent method because of the convexity in the optimization. The stochastic gradient descent method may enhance computational efficiency given a large amount of data. The impact determination engine 450 may determine the healthcare related parameters for each healthcare provider using a non-negative least square problem with L-2 regularization solved by an active set method.

The impact determination engine 450 may sequentially iterate determining the healthcare provider related parameters and determining the patient related parameters until a threshold is satisfied. For example, the impact determination engine 450 may repeat the process one thousand times or some other predetermined number of times based on processing usage limits. In another example, the impact determination engine 450 may repeat the process until the difference between prior parameters for the joint patient-healthcare provider impact model and current parameters for the joint patient-healthcare provider impact model have satisfied a difference threshold. For example, once the values of the parameters change less than 0.001% the impact determination engine 450 may determine that any additional accuracy in estimation is outweighed by processing power required to repeat the process in stop repeating the process and use the current values as the impacts of notifications.

The impact determination engine 450 may initially begin with determining the patient impact model instead of a healthcare provider impact model as there may be more discrete samples for patients than for healthcare providers, and having more discrete samples initially may result in a more accurate initial estimate. A more accurate initial estimate may result in a more accurate final estimate for a given number of iterations, or result in fewer iterations needed until a difference threshold is satisfied and thus reducing processing needed to determine the impact of the notifications.

In some implementations, the impact determination engine 450 may use a machine-learning graphical model to output a joint patient-healthcare provider impact model. For example, the impact determination engine 450 may provide the notification records and indications of relationships identified between the healthcare providers and the anonymized patients to a machine-learning graphical model to output a joint patient-healthcare provider impact model.

The plan generator 470 may obtain the impacts of notifications determined by the impact determination engine 450 and notification constraints 460, and generate a notification plan. For example, the plan generator 470 may determine to provide one million of a particular type of notification to potential patients and two million of another type of notification to healthcare providers to increase a forecasted number of treatments. The plan generator 470 may determine the notification plan based on notification constraints 460. The notification constraints 460 may include specifications of one or more of a budget, notification types available, notifications provided so far, notifications allocated, a minimum number of notifications for each type, a maximum number of notifications of each type, a remaining number of notifications to provide for each type, a cost for each type of notification, an available budget for each type of notification, or a total budget for a type of notification. For example, the notification constraints 460 may specify that a total of one million is available for notifications, three types of notifications are available, a first type of notification costs fourteen dollars per million provided, a second type of notification costs eighteen dollars per million provided, and a third type of notification costs sixteen dollars per million provided, and in response, based on the impacts of notifications, the plan generator 470 may determine to allocate two hundred thousand dollars to the first type of notification, five hundred thousand dollars to the second type of notification, and three hundred thousand dollars to the third type of notification.

The plan generator 470 may receive the notification constraints from a user. For example, the plan generator 470 may provide a graphical user interface for a user to input the notification constraints and change the notification constraints, and in response may update the notification plan and display the updated notification plan to the user through the graphical user interface.

In some implementations, the plan generator 470 may receive indications of events and in response update a notification plan. For example, the plan generator 470 may receive an indication that a flu epidemic is spreading, and in response, may determine to increase a number of allocations of a particular type of notification and decrease a number of allocations of another type of notification.

The notification scheduler 490 may obtain a notification plan generated by the plan generator 470 and provide notifications to recipients based on the notification plan. For example, the notification scheduler 490 may automatically provide those notification to the recipients according to the notification plan. In another example, the plan generator 470 may display the notifications to a user of the system 400 for a user to determine whether to provide notifications according to the notification plan.

Figure 5:
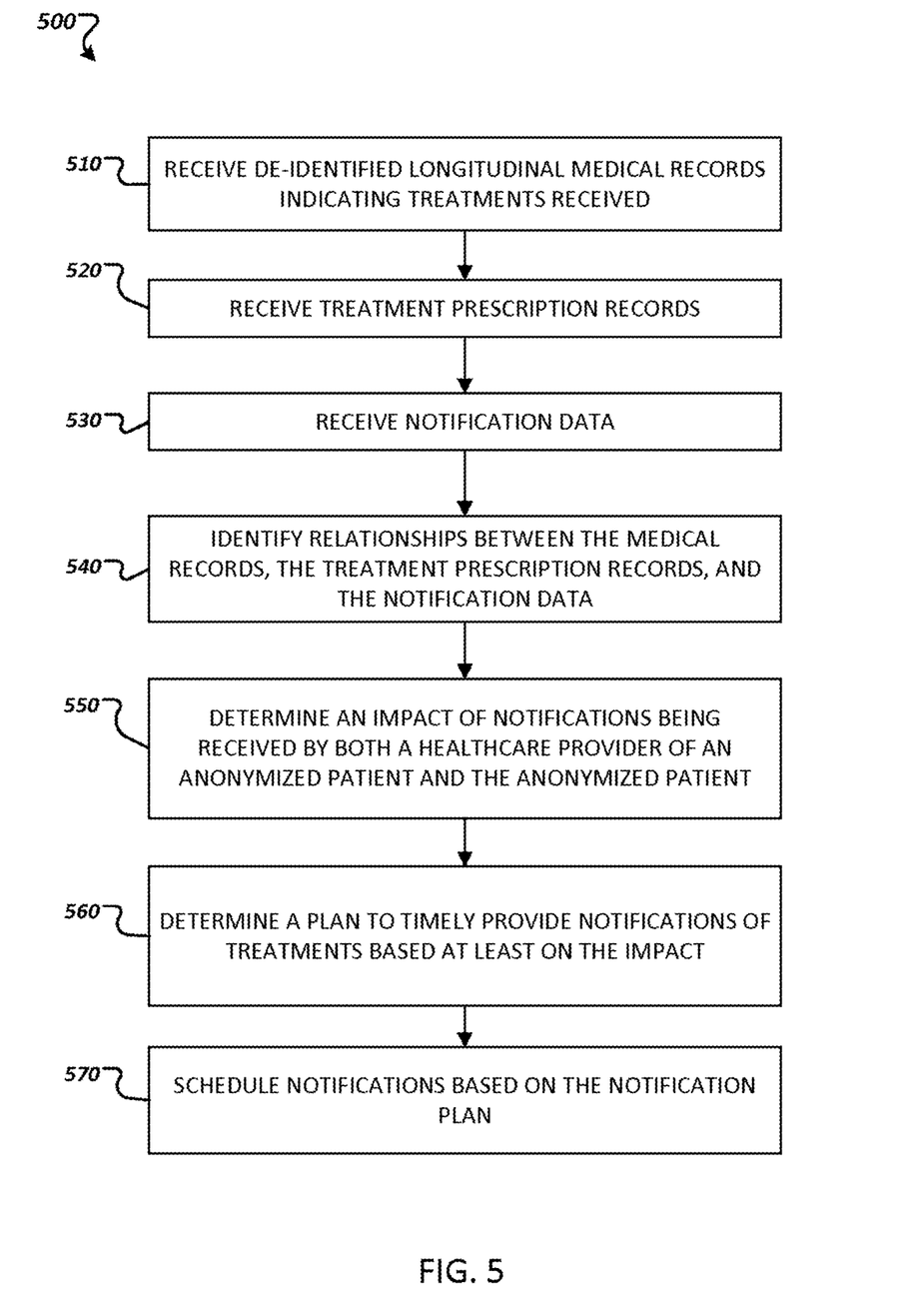
FIG. 5 illustrates an example of a flow chart for providing timely notifications of treatments to healthcare providers and patients.

FIG. 5 illustrates an example of a flow chart 500 for providing timely notifications of treatments to healthcare providers and patients. Initially, de-identified longitudinal medical records are received (510). For example, the relationship identifier 440 may receive de-identified longitudinal medical records from a database of a pharmacy or drugstore. Before, after, or in parallel, treatment prescription records (520) and notification data are received (530). For example, the relationship identifier 440 may receive treatment prescription records from a database of a doctor's office and notification data from a database of a notification provider.

Thereafter, relationships between the medical records, the treatment prescription records, and the notification data may be identified (540). For example, the relationship identifier 440 may determine that a particular medical record indicates that an anonymized patient received a particular treatment, determine that a particular notification record indicates that a recipient received a notification for the particular treatment, determine that the particular medical record has an identifier, that refers to an anonymized patient, that is the same identifier representing a recipient that is associated with the particular notification record, determine that a particular notification record indicates that another recipient that is a healthcare provider received another notification for the particular treatment, and determine that the prescription record indicates that the healthcare provider prescribed the treatment to the anonymized patient.

An impact of the notifications being received by both a healthcare provider of an anonymized patient and the anonymized patient may be determined based on the identified relationships (550). For example, the impact determination engine 450 may determine a patient impact model, then determine healthcare provider parameters of a joint patient-healthcare model using patient parameters from the patient impact model, then determine updated patient parameters of the joint patient-healthcare model using the healthcare provider parameters, and iterate determining parameters of the joint patient-healthcare model as appropriate. Next, a plan for timely notifying may be determined based on the determined impacts (560). For example, the plan generator 470 may receive the forecast model and notification constraints specified by a user indicating types of notifications available and constraints on providing the notifications, and in response, determine a notification plan indicating how many of each type of notification should be provided to recipients that include potential patients and healthcare providers. Finally, notifications may be scheduled based on the notification plan (570). For example, the notification scheduler 490 may automatically provide a first type of notification using a first channel to potential patients and a second type of notification using a second channel to healthcare providers according to the notification plan.

Figure 6:
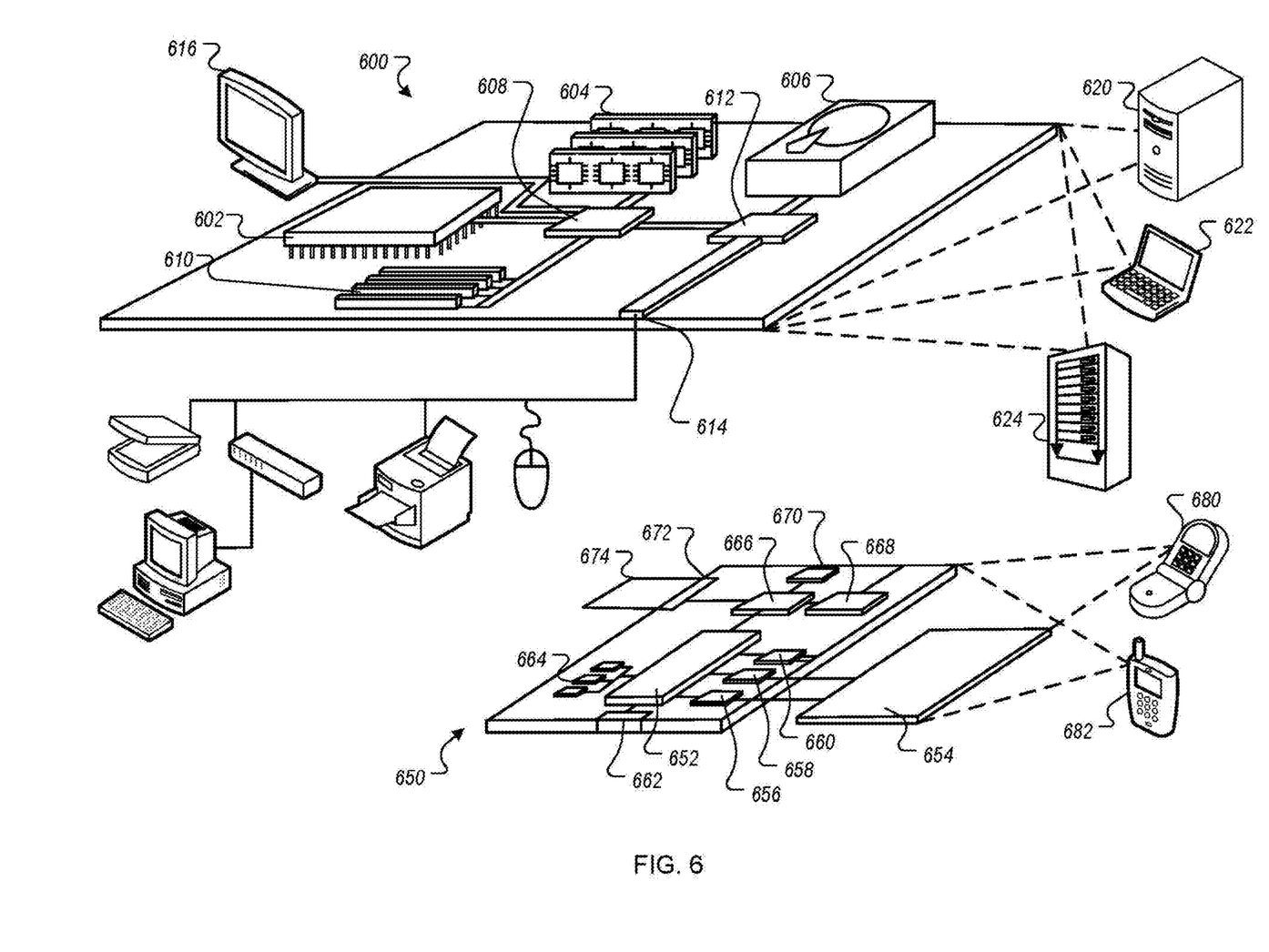
FIG. 6 shows a block diagram of a computing system that can be used in connection with computer-implemented methods described in this specification.

FIG. 6 is a block diagram of computing devices 600, 650 that may be used to implement the systems and methods described in this document, either as a client or as a server or plurality of servers. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a computer-readable medium. In one implementation, the memory 604 is a volatile memory unit or units. In another implementation, the memory 604 is a non-volatile memory unit or units.

The storage device 606 is capable of providing mass storage for the computing device 600. In one implementation, the storage device 606 is a computer-readable medium. In various different implementations, the storage device 606 may be a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 604, the storage device 606, or memory on processor 602.

The high-speed controller 608 manages bandwidth-intensive operations for the computing device 600, while the low speed controller 612 manages lower bandwidth-intensive operations. Such allocation of duties is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can process instructions for execution within the computing device 650, including instructions stored in the memory 664. The processor may also include separate analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD display or an OLED display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provided in communication with processor 652, so as to enable near area communication of device 650 with other devices. External interface 662 may provide, for example, for wired communication (e.g., via a docking procedure) or for wireless communication (e.g., via Bluetooth or other such technologies).

The memory 664 stores information within the computing device 650. In one implementation, the memory 664 is a computer-readable medium. In one implementation, the memory 664 is a volatile memory unit or units. In another implementation, the memory 664 is a non-volatile memory unit or units. Expansion memory 674 may also be provided and connected to device 650 through expansion interface 672, which may include, for example, a SIMM card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provided as a security module for device 650, and may be programmed with instructions that permit secure use of device 650. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS receiver module 670 may provide additional wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

As discussed above, systems and techniques described herein can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Further to the descriptions above, a user may be provided with controls allowing the user to make an election as to both if and when systems, programs or features described herein may enable collection of user information (e.g., information about a user's social network, social actions or activities, profession, a user's preferences, or a user's current location), and if the user is sent content or communications from a server. In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. For example, various forms of the flows shown above may be used, with steps re-ordered, added, or removed. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A computer-implemented method to timely provide notifications of treatments, the method comprising:
    generating, based on machine-learning techniques, a graphical model that processes data about a plurality of notification records and treatment data comprising de-identified records identifying a treatment received by a patient as being prescribed to the patient by a healthcare provider, each de-identified record including an identifier that uniquely distinguishes the patient from other patients, wherein:

each notification record in the plurality of notification records is associated with a respective notification for the treatment and identifies a respective channel through which the notification for the treatment was provided, and the respective channel provides data indication a recipient of the notification;

learning, by the graphical model, a function that identifies relationships between treatments for the patient and each notification received by a recipient, wherein the function is based on values computed for variables in at least the treatment data processed by the graphical model;

computing, based at least on the graphical model and the function, an impact parameter that indicates whether notifications received by the healthcare provider and the patient resulted in i) the healthcare provider prescribing the treatment to the patient and ii) the patient receiving the treatment prescribed by the healthcare provider; and determining, based on the impact parameter, a plan comprising a timing of notifications that causes an increase or prescribed treatments received by a plurality of patients and a reduction in usage of processing and storage resources of a system that includes the graphical model.

2. The method of claim 1, comprising:
identifying a first identifier that uniquely distinguishes the patient from other anonymized patients in a de-identified longitudinal medical record; and
determining that the first identifier matches a second identifier that uniquely distinguishes the patient from other anonymized patients in a treatment prescription record.

3. The method of claim 1, wherein the graphical model represents a patient impact model and the method comprises:
determining healthcare provider related parameters for a joint patient-healthcare provider impact model using the patient impact model, the plurality of notification records, and treatment prescription records of the healthcare providers; and
determining patient related parameters for the joint patient-healthcare provider impact model using the plurality of notification records, the de-identified records, and the healthcare provider related parameters.

4. The method of claim 3, wherein determining the healthcare provider related parameters and the patient related parameters are sequentially iterated multiple times.

5. The method of claim 1, comprising:
providing the plurality of notification records, information indicating relationships identified between a plurality of healthcare providers and anonymized patients to the graphical model to output a joint patient-healthcare provider impact model.

6. The method of claim 1, wherein determining the plan comprises:
obtaining information describing notification constraints;
obtaining information describing computing resources necessary to provide notifications through respective channels to patients;
obtaining information describing resources necessary to provide notifications through respective channels to healthcare providers; and
determining the plan based at least on the information describing notification constraints, information describing resources necessary to provide notifications through respective channels to patients, the information describing resources necessary to provide notifications through respective channels to healthcare providers, and the impact parameter.

7. The method of claim 1, comprising: receiving prescription records of the healthcare provider in response to providing a request for prescription records of healthcare providers with particular attributes.

8. The method of claim 1, comprising:
receiving de-identified longitudinal medical records in response to providing a request for de-identified longitudinal medical records of patients with particular attributes.

9. The method of claim 1, wherein the notification records encode information identifying notifications provided through channels including a digital channel and a non-digital channel.

10. The method of claim 1, comprising:
scheduling, based at least on the plan, a first set of notifications to be provided through respective channels to only the patients, a second set of notifications to provided through respective channels to only the healthcare providers, and a third set of notifications to be provided to both the healthcare providers and the patients.

11. A system comprising one or more computers and one or more storage devices storing instructions that are operable, when executed by the one or more computers, to cause the one or more computers to perform operations comprising:
generating, based on machine-learning techniques, a graphical model that processes data about a plurality of notification records and treatment data comprising de-identified records identifying a treatment received by a patient as being prescribed to the patient by a healthcare provider, each de-identified record including an identifier that uniquely distinguishes the patient from other patients, wherein,
each notification record in the plurality of notification records is associated with a respective notification for the treatment, and identifies a respective channel through which the notification for the treatment eras provided, and
the respective channel provides data indicating a recipient of the notification;
learning, by the graphical model, a function that identifies relationships between treatments for the patient and each notification received by a recipient, wherein the function is based on values computed for variables in at least the treatment data processed by the graphical model;
computing, based at least on the graphical model and the function, an impact parameter that indicates whether notifications received by the healthcare provider and the patient resulted in: i) the healthcare provider prescribing the treatment to the patient and ii) the patient receiving the treatment prescribed by the healthcare provider; and
determining, based on the impact parameter, a plan comprising a timing of notifications that causes an increase of prescribed treatments received by a plurality of patients and a reduction in usage of processing and storage resources of a system that includes the graphical model.

12. The system of claim 11, wherein the operations comprise:

identifying a first identifier that uniquely distinguishes the patient from other anonymized patients in a de-identified longitudinal medical record; and determining that the first identifier matches a second identifier that uniquely distinguishes the patient from other anonymized patients in a treatment prescription record.

13. The system of claim 11, wherein the graphical model represents a patient impact model and the operations comprises:
   determining healthcare provider related parameters for a joint patient-healthcare provider impact model using the patient impact model, the plurality of notification records, and treatment prescription records of the healthcare providers; and
   determining patient related parameters for the joint patient-healthcare provider impact model using the plurality of notification records, the de-identified records, and the healthcare provider related parameters.

14. The system of claim 13, wherein determining the healthcare provider related parameters and the patient related parameters are sequentially iterated multiple times.

15. The system of claim 11, wherein the operations comprise:
   providing the plurality of notification records, information indicating relationships identified between a plurality of healthcare providers and anonymized patients to the graphical model to output a joint patient-healthcare provider impact model.

16. The system of claim 11, wherein determining the plan comprises:
   obtaining information describing notification constraints;
   obtaining information describing computing resources necessary to provide notifications through respective channels to patients;
   obtaining information describing resources necessary to provide notifications through respective channels to healthcare providers; and
   determining the plan based at least on the information describing notification constraints, information describing resources necessary to provide notifications through respective channels to patients, the information describing resources necessary to provide notifications through respective channels to healthcare providers, and the impact parameter.

17. The system of claim 11, wherein the operations comprise:
   receiving prescription records of the healthcare provider in response to providing a request for prescription records of healthcare providers with particular attributes.

18. The system of claim 11, wherein the operations comprise:
   receiving de-identified longitudinal medical records response to providing a request for de-identified longitudinal medical records of patients with particular attributes.

19. The system of claim 11, wherein the notification records encode information identifying notifications provided through channels including a digital channel and a non-digital channel.

20. A non-transitory computer-readable medium storing software comprising instructions executable by one or more computers which, upon such execution, cause the one or more computers to perform operations comprising:
   generating, based on machine-learning techniques, a graphical model that processes data about a plurality of notification records and treatment data comprising de-identified records identifying a treatment received by a patient as being prescribed to the patient by a healthcare provider, each de-identified record Including an Identifier that uniquely distinguishes the patient from other patients, wherein:
      each notification record in the plurality of notification records is associated with a respective notification for the treatment and identifies a respective channel through which the notification for the treatment was provided, and
      the respective channel provides data indicating a recipient of the notification;
   learning, by the graphical model, a function that identifies relationships between treatments for the patient and each notification received by a recipient, wherein the function is based on values computed for variables in at least the treatment data processed by the graphical model;
   comprising, based at least on the graphical model and the function, an impact parameter that indicates whether notifications received by the healthcare provider and the patient resulted in: i) the healthcare provider prescribing the treatment to the patient and ii) the patient receiving the treatment prescribed by the healthcare provider; and
   determining, based on the impact parameter, a plan comprising a timing of notifications that causes an increase of prescribed treatments received by a plurality of patients and a reduction in usage of processing and storage resources of a system that includes the graphical model.

* * * * *

UNITED STATES PATENT AND TRADEMARK OFFICE
CERTIFICATE OF CORRECTION

PATENT NO. : 10,937,531 B1  
APPLICATION NO. : 15/948006  
DATED : March 2, 2021  
INVENTOR(S) : Yunlong Wang et al.

Page 1 of 1

It is certified that error appears in the above-identified patent and that said Letters Patent is hereby corrected as shown below:

On the Title Page

Item (54), delete "PATIENT" and insert --PATIENTS--.

In the Specification

Column 1, Line 3, delete "PATIENT" and insert --PATIENTS--.

In the Claims

Column 19, Line 6, Claim 1, delete "indication" and insert --indicating--.

Column 19, Line 17, Claim 1, delete "in" and insert --in:--.

Column 19, Line 23, Claim 1, delete "or" and insert --of--.

Column 20, Line 39, Claim 11, delete "wherein," and insert --wherein:--.

Column 20, Line 42, Claim 11, delete "treatment," and insert --treatment--.

Column 20, Line 43, Claim 11, delete "eras" and insert --was--.

Column 22, Line 4, Claim 18, before "response" insert --in--.

Column 22, Line 20, Claim 20, delete "Including" and insert --including--.

Column 22, Line 21, Claim 20, delete "Identifier" and insert --identifier--.

Column 22, Line 36, Claim 20, delete "comprising," and insert --computing,--.

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*